(12) United States Patent
Wiest et al.

(10) Patent No.: US 7,412,902 B2
(45) Date of Patent: Aug. 19, 2008

(54) DEVICE FOR DETERMINATION AND/OR MONITORING OF THE VOLUMETRIC AND/OR MASS FLOW OF A MEDIUM AND HAVING COUPLING ELEMENT INCLUDING TWO ELEMENT PORTIONS

(75) Inventors: Achim Wiest, Weil am Rhein (DE); Andreas Berger, Therwil (CH); Torsten Strunz, Basel (CH)

(73) Assignee: Endress + Hauser Flowted AG, Reinach (CH)

( * ) Notice: Subject to any disclaimer, the term of this patent is extended or adjusted under 35 U.S.C. 154(b) by 1 day.

(21) Appl. No.: 10/551,220

(22) PCT Filed: Mar. 31, 2004

(86) PCT No.: PCT/EP2004/003403

§ 371 (c)(1),
(2), (4) Date: Jul. 21, 2006

(87) PCT Pub. No.: WO2004/088252

PCT Pub. Date: Oct. 14, 2004

(65) Prior Publication Data

US 2006/0278015 A1    Dec. 14, 2006

(30) Foreign Application Priority Data

Apr. 1, 2003    (DE) ................ 103 14 916

(51) Int. Cl.
*G01F 1/66*    (2006.01)
(52) U.S. Cl. ................ 73/861.25; 73/861.27

(58) Field of Classification Search .. 73/861.25–861.31
See application file for complete search history.

(56) References Cited

U.S. PATENT DOCUMENTS

| | | | | | |
|---|---|---|---|---|---|
| 3,050,997 | A | * | 8/1962 | Lake | 73/861.27 |
| 3,913,386 | A | * | 10/1975 | Saglio | 73/644 |
| 3,942,358 | A | * | 3/1976 | Pies | 73/611 |
| 4,279,167 | A | * | 7/1981 | Erb et al. | 73/861.25 |
| 6,532,827 | B1 | * | 3/2003 | Ohnishi | 73/861.27 |
| 6,632,827 | B2 | | 10/2003 | McCullough | |

FOREIGN PATENT DOCUMENTS

| | | |
|---|---|---|
| DE | 41 24 692 A1 | 1/1993 |
| EP | 1 235 056 A2 | 8/2002 |
| EP | 1 248 081 A1 | 10/2002 |
| GB | 2 363 455 A | 12/2001 |
| JP | 61054445 A | 3/1986 |
| WO | WO 02/39069 A | 5/2002 |

\* cited by examiner

*Primary Examiner*—Harshad Patel
(74) *Attorney, Agent, or Firm*—Bacon & Thomas, PLLC

(57) ABSTRACT

A clamp-on ultrasonic flow measuring device for determining volume and/or mass flow rate of a medium in a containment. The clamp-on ultrasonic measuring device is of low temperature sensitivity. To this end, the coupling element, through which the ultrasonic measuring signals are coupled into, and/or out of, the containment, has at least two element portions, which are embodied and/or arranged in such a manner that the predetermined in-coupling angle into the containment and/or the predetermined out-coupling angle out of the containment are/is approximately constant over an extended temperature range.

6 Claims, 2 Drawing Sheets

DEVICE FOR DETERMINATION AND/OR MONITORING OF THE VOLUMETRIC AND/OR MASS FLOW OF A MEDIUM AND HAVING COUPLING ELEMENT INCLUDING TWO ELEMENT PORTIONS

FIELD OF THE INVENTION

The invention relates to an apparatus for determining and/or monitoring the volume and/or mass flow rate of a medium in a containment, especially in a pipe. The apparatus includes: at least one ultrasonic transducer, which emits and/or receives ultrasonic measuring signals; associated with the ultrasonic transducer, a coupling element, via which the ultrasonic measuring signals are coupled into, and out of, the containment at a predetermined in-coupling/out-coupling angle; and a control/evaluation unit, which, on the basis of the measuring signals, or on the basis of measurement data derived from the measuring signals, determines the volume and/or mass flow rate of the medium flowing in the containment.

BACKGROUND OF THE INVENTION

Ultrasonic flow measuring devices are applied often in process and automation technology. They make possible contactless determination of the volume and/or mass flow rate of a medium in a pipeline.

Known ultrasonic flow measuring devices work either by the Doppler principle or the travel-time-difference principle. In the case of the travel-time-difference principle, the different travel times of the ultrasonic measuring signals in the direction of flow, and counter to the direction of flow, of the medium are exploited. To this end, the ultrasonic measuring signals are alternatingly issued, respectively received, in the direction of flow, and counter to the direction of flow, of the medium. On the basis of the travel-time-difference of the ultrasonic measuring signals, the flow velocity can be determined, and, with that and known diameter of the pipe, the volume flow rate of the medium, or, with known density, the mass flow rate of the medium.

In the case of the Doppler principle, ultrasonic measuring signals of predetermined frequency are coupled into the flowing medium. The ultrasonic measuring signals reflected in the medium are evaluated. On the basis of a frequency shift occurring between the ultrasonic measuring signal which was coupled into the medium and the reflected ultrasonic measuring signal, likewise the flow velocity of the medium, or the volume and/or mass flow rate, can be determined.

The use of flow measuring devices working according to the Doppler principle is only possible, when present in the medium are air bubbles or impurities, on which the ultrasonic measuring signals are reflected. Thus, use of ultrasonic flow measuring devices using the Doppler principle is rather limited, compared to ultrasonic flow measuring devices using the travel-time-difference principle.

With respect to types of measuring devices, a distinction is drawn between ultrasonic flow measuring pickups, which are inserted into the pipeline, and clamp-on flow measuring devices, where the ultrasonic transducers are pressed onto the pipeline externally by means of a clamp connection. Clamp-on flow measuring devices are described, for example, in EP 0 686 255 B1, U.S. Pat. No. 4,484,478 or U.S. Pat. No. 4,598,593.

In the case of the two types of ultrasonic flow measuring devices, the ultrasonic measuring signals are radiated at a predetermined angle into, and/or received from, the pipeline, or measuring tube, as the case may be, containing the flowing medium. In order to achieve an optimum impedance matching, the ultrasonic measuring signals are coupled into, or out of, the pipeline via a lead-in member, or a coupling wedge, as the case may be. Principal component of an ultrasonic transducer is at least one piezoelectric element, which produces and/or receives the ultrasonic measuring signals.

The ultrasonic measuring signals produced in a piezoelectric element are led via the coupling wedge, or lead-in member, as the case may be, and, in the case of a clamp-on flow measuring device, through the pipe wall, into the liquid medium. Since the velocities of sound in a liquid and in plastic differ from one another, the ultrasonic waves are refracted at the transition from one medium into the other. The angle of refraction at the transition from one medium into another medium is dependent on the ratio of the velocities of sound $c_m$, $c_n$ in the two media n, m.

Mathematically, Snell's law can preferably be expressed according to the following formula:

$$c_n/\sin \alpha_n = c_m/\sin \alpha_m = \text{const.} \quad (1)$$

where:

$c_n$ is the velocity of sound e.g. in the coupling wedge made, for example, of plastic;

$c_m$ is the velocity of sound e.g. in the medium, which is, for example, water;

$\alpha_n$ is the angle between the sound path and the normal to the bounding surface of the coupling wedge at the point where the ultrasonic measuring signal passes through the bounding surface; and $\alpha_m$ is the angle between the sound path and the normal to the bounding surface of the medium at the point where the ultrasonic measuring signal passes through the bounding surface.

With coupling wedges, or lead-in members, of plastic, among other things, a good impedance matching can be achieved; however, the velocity of sound in plastic has a relatively strong temperature dependence. Typically, the velocity of sound in plastic changes from about 2500 m/s at 25° C. to about 2200 m/s at 130° C. In addition to the change of travel time of ultrasonic measuring signals in the plastic of the coupling wedge brought about by temperature, the direction of propagation of the ultrasonic measuring signals in the flowing medium also changes. Both changes, in the case of an ultrasonic flow measuring device operating according to the travel time difference method, naturally act unfavorably on the accuracy of measurement. Added to this is the fact that the propagation velocity exhibits, in certain media, likewise a strong temperature dependence.

For coping with the temperature dependence of the coupling wedges, it is known from WO 02/39069 A2 to construct the coupling element out of a plurality of segments in the form of circular arcs. Preferably, the segments are made of metal. The individual segments are arranged separated from one another and they extend from a contact plane, which faces the piezoelectric element, out to a base plate, which is connected with the pipe wall. The length of the individual segments is, in such case, so measured, that the ultrasonic measuring signals are radiated and received at a predetermined angle at the base plate. This embodiment is, however, relatively complex.

SUMMARY OF THE INVENTION

An object of the invention is to provide a clamp-on ultrasonic measuring device, whose measuring accuracy is relatively insensitive to temperature changes of the medium and/or of the environment.

The object is solved by providing the coupling element with at least two element portions, which are embodied and/or arranged in such a manner that the predetermined in-coupling angle into the containment, or the predetermined out-coupling angle out of the containment, is approximately independent of the temperature of the coupling wedge over an extended range of temperature. "Extended range of temperature" means here at least the temperature range of about 0° C. to 130° C.

An advantageous further development of the apparatus of the invention concerns the case where the velocity of sound in the medium being measured itself exhibits a relatively strong temperature dependence and where the temperature of the medium changes in step with the temperature of the coupling wedge. In this case, in agreement with Snell's law, the in-coupling, or out-coupling, angle of the ultrasonic measuring signals is determined also by the temperature dependence of the velocity of sound in the medium. In order to keep the in-coupling angle into the medium, or the out-coupling angle out of the medium, in accordance with the invention, essentially constant over an extended range of temperature, the materials and the dimensions of the at least two element portions of the coupling element are so selected that, in effect, no change of the incidence/reflection angle occurs, which would negatively influence the measurement result within desired tolerance limits. In the case of this solution, one is dealing with a medium-specific solution.

BRIEF DESCRIPTION OF THE DRAWINGS

The invention will now be explained in greater detail on the basis of the drawings, the figures of which show as follows.

DESCRIPTION OF THE PREFERRED EMBODIMENTS

In a preferred embodiment of the apparatus of the invention, the coupling element comprises at least two coupling wedges, which are successively traversed by the ultrasonic measuring signals. Preferably, the coupling wedges are made of plastics with different sound velocities.

The element portions, or the coupling wedges, as the case may be, comprise, in an advantageous embodiment of the apparatus of the invention, different materials, with the materials being selected such that temperature-related changes of sound velocity, or the index of refraction, of a first element portion, or a first coupling element, as the case may be, are at least approximately compensated by temperature-related changes of sound velocity, or index of refraction, of at least a second element portion, or a second coupling wedge, as the case may be. Preferably, the compensation occurs over as great a temperature range as possible.

In an alternative embodiment of the apparatus of the invention, a plurality of element portions, or a plurality of mutually connected coupling wedges, as the case may be, of different materials are provided, with the materials being so selected that temperature-related changes of sound velocity, or index of refraction, of the medium and temperature-related changes of the sound velocities, or indices of refraction, in the at least two element portions, or coupling wedges, essentially mutually compensate one another.

With this embodiment, the influence of temperature fluctuations of the medium on the in-coupling, or out-coupling, angle can be directly eliminated, or the effects can be kept so small, that the measurement accuracy is only insignificantly degraded.

In an advantageous embodiment of the apparatus of the invention, it is provided that the path lengths, which the ultrasonic measuring signals trace in the element portions of the coupling wedges, or the lead-in members, are so selected, that the sum of the corresponding travel times, which the ultrasonic measuring signals require for traversing the element portions, is at least approximately constant over a predetermined temperature range. This is achieved preferably by the appropriately selected dimensioning of the element portions. This embodiment assures that, almost independently of temperature changes, always the maximum signal amplitude of an ultrasonic measuring signal is received from each ultrasonic transducer. More or less complex readjustments of the ultrasonic transducers on the pipe due to temperature changes in the sensors are, consequently, not required.

Figure 1:
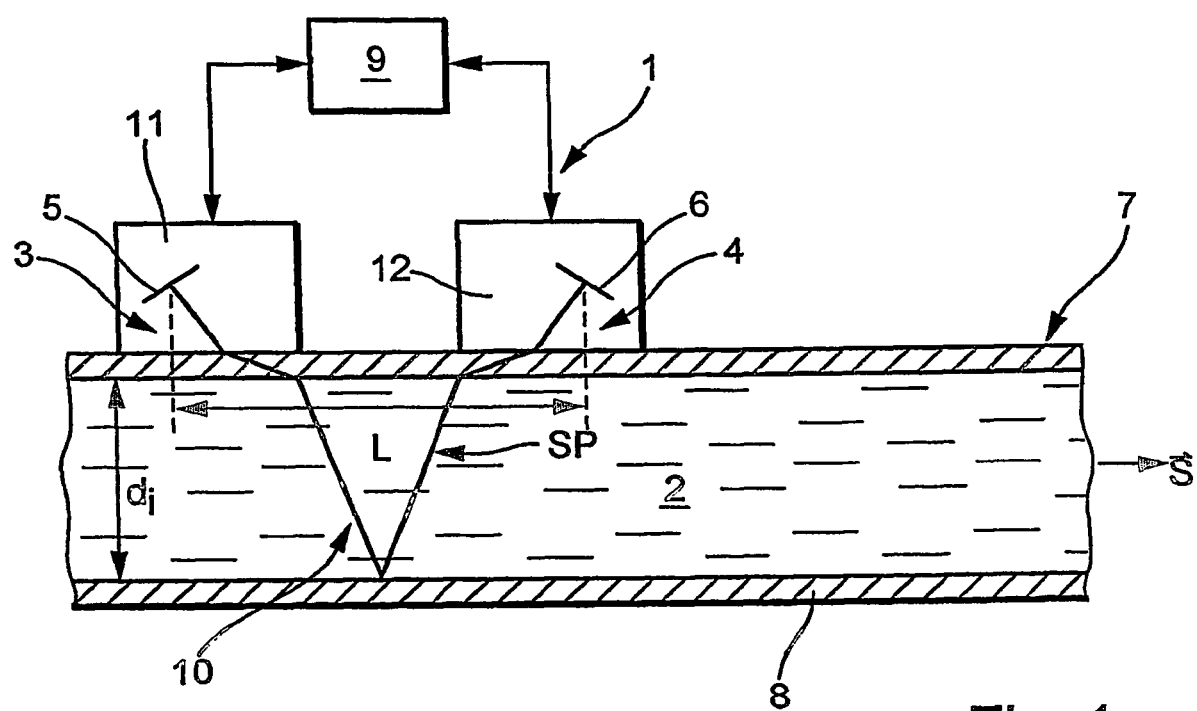
FIG. 1 a schematic drawing of a clamp-on ultrasonic flow measuring device in two-traverse mode.

FIG. 1 is a schematic presentation of a clamp-on flow measuring device 1 in two-traverse mode 10. The flow measuring device 1 determines volume flow rate and/or mass flow rate of the medium 2 in the pipe 7 using the known travel-time-difference method.

Essential components of the clamp-on ultrasonic flow measuring device 1 are the two ultrasonic transducers 3, 4 and the control/evaluation unit 9. The two ultrasonic transducers 3, 4 are attached to the pipe 7 by means of a securement apparatus not separately shown in the figure. Appropriate securement apparatuses are sufficiently known in the state of the art and are also available from the assignee. Medium 2 flows through pipe 7 of predetermined inner diameter di in the stream direction S.

An ultrasonic transducer 3; 4 includes, as essential components: At least one piezoelectric element 5; 6, which produces and/or receives the ultrasonic measuring signals; and a coupling wedge, or lead-in element, 11; 12. The ultrasonic measuring signals are coupled via the coupling wedges 11, 12 into, and out of, the pipe 7 containing the flowing medium 2. The coupling wedges 11; 12 determine the directions of the ultrasonic measuring signals into and out of the pipe and medium; additionally, they serve for optimizing the impedance matching of the ultrasonic measuring signals at the transition into and out of the pipe 7.

The two ultrasonic transducers 3, 4 are positioned at a separation L from one another, with the separation L being selected such that an as high as possible energy fraction of the ultrasonic measuring signals sent from an ultrasonic transducer 3; 4 is received in the respective other ultrasonic transducer 4; 3. The optimum positioning depends on a number of different system and/or process variables. These system and process variables include, for example, the inner diameter di of the pipe 7, the thickness of the pipe wall 8, the velocity of sound $c_3$ in the material of which the pipe is made, or the velocity of sound $C_4$ in the medium 2. Additionally to be considered is that the velocities of sound in the different materials, such as the materials of the coupling wedge, pipe wall and medium, exhibit various degrees of temperature dependence.

In the illustrated case, the separation L of the two ultrasonic transducer 3, 4 is so selected that the ultrasonic measuring signals, which, according to the travel-time-difference method, are alternately emitted and received from and by the two ultrasonic transducers 3, 4, propagate via the sound path SP in the pipe 7 containing the flowing medium 10. Sound path SP exhibits two traverses, thus two crossings of the pipe 7. The traverses can be diametral or chordal.

Figure 2:
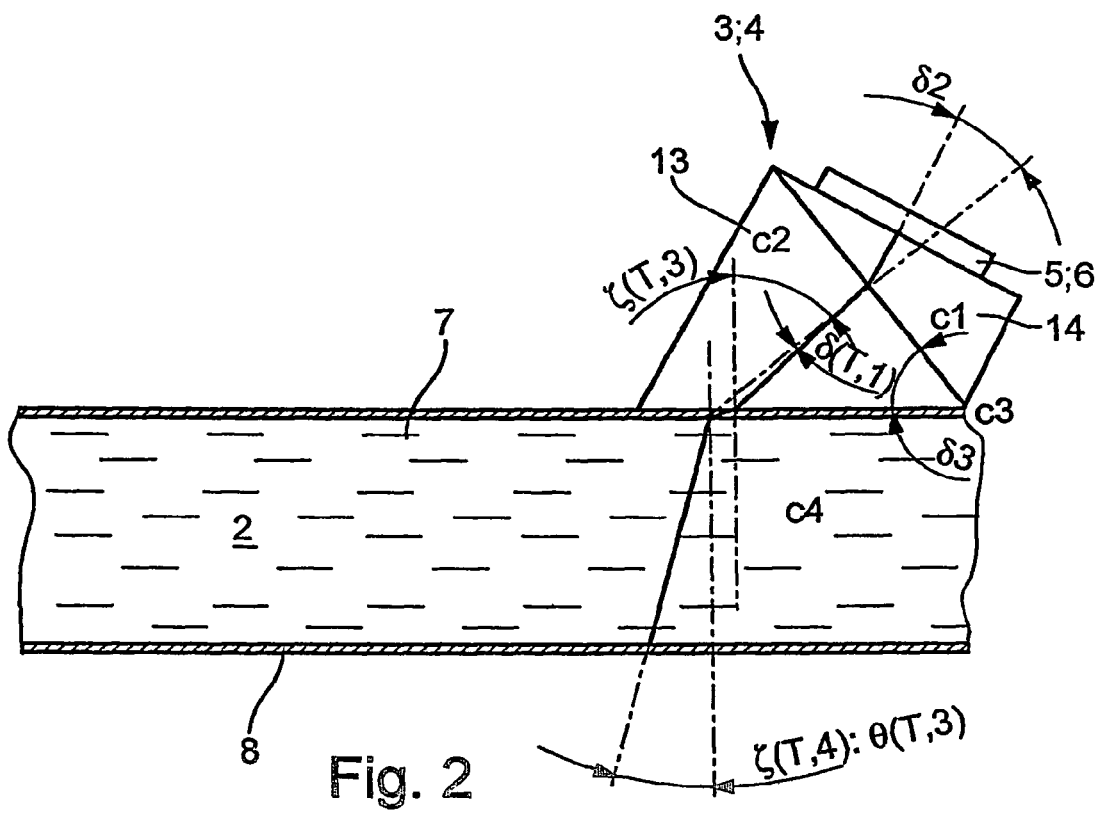
FIG. 2 a longitudinal section through a form of embodiment of the ultrasonic transducer of the invention.

FIG. 2 shows, in section, a form of embodiment of the ultrasonic transducer 3; 4. The coupling element 11; 12, according to the invention, is composed of at least two element portions 13, 14, which are successively traversed by the ultrasonic measuring signals emitted from, or received by, the piezoelectric element 5; 6.

Consider first the case in which the electronic measuring signals are coupled into, or out of, pipe 7 on the basis of element portion 13 alone. The in-coupling, out-coupling angle is essentially determined by the geometry of the element portion 13, i.e. the geometry of element portion 13 is so chosen, that as much energy as possible passes through the boundary surface between the element portion 13 and the pipe containing the flowing medium 2. The in-coupling and out-coupling of a high energy fraction of the ultrasonic measuring signal is of decisive importance for a good measurement accuracy. In order to achieve the reliable measurement results over any long period of time, it is, moreover, important that a determined, optimized in-coupling/out-coupling angle also subsequently remains constant. As indicated every deviation from the predetermined value leads to a degrading of the measurement accuracy. The permanent keeping of the incidence/reflection angle of the measuring signal is especially problematic, because velocities of sound in the different materials change in varying degrees as a function of temperature.

This is where the solution of the invention comes in: By adding a second element portion 14, whose sound velocity differs from the sound velocity of the first element portion 13, it becomes possible to compensate, at least approximately, and, in the ideal case, completely, the temperature dependence of the coupling element 11; 12, or lead-in member. Of course, the coupling element 11; 12 of the invention can also be constructed of more than two element portions 13, 14. These can be embodied such that the temperature-dependent angle of refraction of an individual element portion 13; 14 is opposed to the sum of the temperature-dependent angles of refraction of all remaining element portions of the coupling element 11; 12.

In principle, equally significant is the case that, in addition to the temperature dependence of the sound velocities of the coupling elements 11, 12, also the velocity of sound in the medium 2 has a strong temperature dependence. By way of example, let water be here the medium 2. In such an application, the coupling element 11; 12, composed of at least two element portions 13, 14, is so embodied that it compensates, at least approximately, the influence of temperature changes of the water on the in-coupling, or out-coupling, angle of the ultrasonic measuring signals over an appropriately large temperature range.

In order to determine the suitable angles in the element portions 13, 14 of the coupling element 11; 12, the sound path SP can be calculated for a temperature range or for individual reference temperatures (in the illustrated case: 25° C.) and the incidence/reflection angle in the medium to be measured, e.g. in water, kept at as constant a value as possible. Additionally, also the entrance position into the medium 2 to be measured and the exit position from the medium to be measured are dependent on the incidence/reflection angles in the element portions 13, 14. In order to keep the temperature influence in the ultrasonic transducers as small as possible, the element portions 13, 14 are dimensioned such that the sum of the travel times of the ultrasonic measuring signals through the element portions 13, 14 of the ultrasonic transducers 3, 4 is constant over a wide temperature range.

Mathematically, the dependence of the velocity of sound c in a medium n on temperature can be expressed to a first approximation according to the following equation (2):

$$c_{T,n} = c_{25°\,C.} + \Delta c \cdot T \tag{2}$$

Reference value for the temperature change of the sound velocity is usually the velocity of sound in the medium n at 25° C. Δc in the formula represents the change of the sound velocity c as a function of temperature T.

By successive application of Snell's law, the in-coupling/out-coupling angle ζ in the medium (n=4) flowing in the pipe can be calculated by means of the following formula:

$$\zeta_{T,4} = a\sin\left(\frac{c_{T,4}}{c_{T,2}} \cdot \sin\left(\delta_3 - a\sin\left(\frac{c_{T,2}}{c_{T,1}} \cdot \sin\delta_2\right)\right)\right) \tag{3}$$

where:

T is temperature;

c(T,n) is the velocity of sound in the different materials, with the indices n=1 . . . 4 representing 1 the compensating wedge, i.e. the second element portion 14;

2 the coupling wedge, i.e. the first element portion 13;

3 the pipe wall 8;

4 the medium 2 flowing in the pipe 7;

$\delta_2$ is the angle of the compensating wedge 14; and $\delta_3$ is the angle of the coupling wedge.

If the temperature of the medium is constant or if the change of the velocity of sound in the medium can be neglected over the temperature range, then the following formula holds:

$$\frac{\sin\left(\delta_3 - a\sin\left(\frac{c_{T,2}}{c_{T,1}} \cdot \sin\delta_2\right)\right)}{c_{T,2}} = const.(T) \tag{4}$$

where:

T is temperature;

c(T,1) is the velocity of sound in the compensation wedge, i.e. in the second element portion 14;

c(T,2) is the velocity of sound in the coupling wedge, i.e. in the first element portion 13;

$\delta_2$ is the angle of the compensation wedge; and $\delta_3$ is the angle of the coupling wedge.

Figure 3:
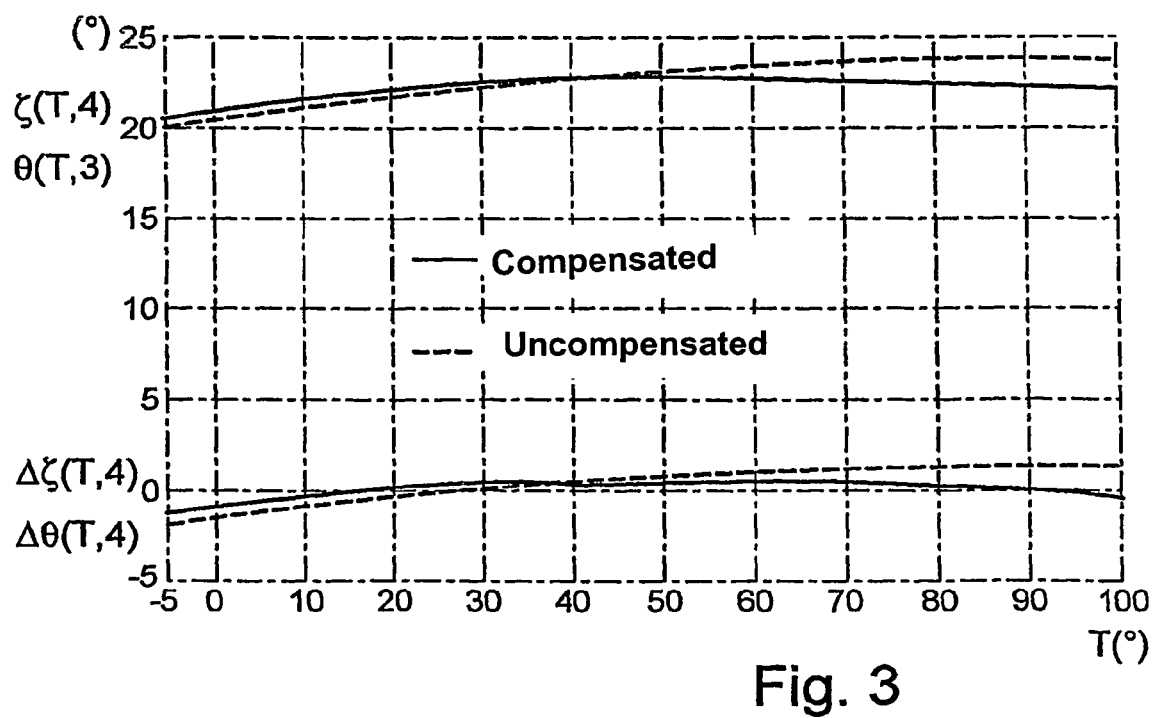
FIG. 3 a graphic presentation of the in-coupling/out-coupling angle as a function of temperature, with and without compensation.

FIG. 3 shows graphically how, by means of the solution of the invention, the influence of temperature on the in-coupling/out-coupling angle ζ in and out of the medium is approximately compensated. In particular, the continuous line represents the temperature dependence of the in-coupling/out-coupling angle ζ of the ultrasonic measuring signal into and out of the medium 2 with compensation; the dashed line shows the corresponding temperature dependence of the incidence/reflection angle θ without the compensation of the invention. Δθ(T,3) represents the corresponding angle change, which occurs in the case of a coupling element 13 without additional compensation wedge 14. Δζ(T,4) is the deviation versus temperature of ζ(T,4) relative to an angle of incidence at 25° C. The measured medium 2 is water in the illustrated case. The first element portion 13 is a plastic with a sound velocity c(25° C.,1) of 2668 m/s and $\Delta c_1$ = −4.5 m/s/K.

In the case of the second element portion 14, such is a plastic with a sound velocity $c(25° C., 2)$ of 2451 m/s and $\Delta c_2 = -0.73$ m/s/K. The curves show that, in the temperature range from 0° C. to 100° C., by adding the second element portion 14 according to the invention (the compensation wedge), the temperature dependence of the angle $\zeta$ of incidence/reflection into/out-of the medium 2 is approximately compensated. To an approximation, the angle $\zeta$ of incidence/reflection in the medium 2 is constant over the entire temperature range in which the ultrasonic flow measuring device 1 is, or can be, used.

The invention claimed is:

1. A clamp-on flowmeter for determining and/or monitoring the volume and/or mass flow rate of a medium in a pipe, comprising:
    two ultrasonic transducers, which emit receive ultrasonic measuring signals;
    coupling elements associated with each of said ultrasonic transducers, via which the ultrasonic measuring signals are coupled into, and out of, the pipe at a predetermined in-coupling and out-coupling angle; and
    a control/evaluation unit, which determines the volume and/or mass flow rate of the medium flowing in the pipe on the basis of the travel-time difference principle; wherein:
    said coupling element includes at least two element portions, which are embodied and/or arranged in such a manner that the influence of temperature changes on a predetermined in-coupling angle ($\zeta$) into the containment and/or on a predetermined out-coupling angle ($\zeta$) out of the containment is approximately compensated in a predetermined, or extended, temperature range, and
    said at least two element portions comprise coupling wedges or lead-in members, the dimensions of said at least two element portions, or the path lengths, which the ultrasonic measuring signals travel in said coupling wedges or said lead-in members, are so selected that the sum of the corresponding travel times, which the ultrasonic measuring signals require for passing through said coupling wedges or said lead-in members, is at least approximately constant over a predetermined temperature range.

2. The apparatus as claimed in claim 1, wherein:
    the in-coupling/out-coupling angle ($\zeta$) of the ultrasonic measuring signals is determined also by the temperature dependence of the medium, said at least two element portions of said coupling element are embodied and/or arranged in such a manner that the in-coupling/out-coupling angle ($\zeta$), respectively, into the medium or out of the medium, is approximately constant over an extended temperature range.

3. The apparatus as claimed in claim 1, wherein:
    said at least two element portions are coupling wedges, which are passed through successively by the ultrasonic measuring signals.

4. The apparatus as claimed in claim 1, wherein:
    said at least two element portions, are made of different materials, wherein the materials are so selected that changes of the velocity of sound ($c2$) in, or the index of refraction of, the material of a first element portion, or of a first coupling wedge, caused by temperature changes are approximately compensated for by changes of the velocity of sound ($c1$) in, or the index of refraction of, at least a second element portion, or of a second coupling wedge, caused by temperature changes.

5. The apparatus as claimed in claim 1, wherein:
    said at least two element portions are made of plastic.

6. The apparatus as claimed in claim 1, wherein:
    a plurality of element portions, of different materials are provided; and
    the materials are so selected that changes of the velocity of sound in, or the index of refraction of, the medium caused by temperatures changes, and changes of the velocities of sound in, or the indices of refraction of, said plurality of element portions, caused by temperature changes, are approximately mutually compensated.

* * * * *